(12) United States Patent
Tamura

(10) Patent No.: US 6,850,593 B1
(45) Date of Patent: Feb. 1, 2005

(54) FLUORESCENT X-RAY ANALYSIS APPARATUS

(75) Inventor: Koichi Tamura, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 359 days.

(21) Appl. No.: 09/531,660

(22) Filed: Mar. 20, 2000

(30) Foreign Application Priority Data

Mar. 18, 1999 (JP) ............................................ 11-073852

(51) Int. Cl.[7] .......................................... G01N 23/223
(52) U.S. Cl. .......................................... 378/49; 378/44
(58) Field of Search .............................. 378/44–45, 71, 378/70, 147, 148, 149, 150, 154, 155, 207, 49, 90, 46

(56) References Cited

U.S. PATENT DOCUMENTS

| 5,408,512 | A | * | 4/1995 | Kuwabara et al. | ........... 378/148 |
| 5,744,813 | A | * | 4/1998 | Kumakhov | .............. 250/505.1 |
| 6,049,588 | A | * | 4/2000 | Cash, Jr. | ...................... 378/147 |

FOREIGN PATENT DOCUMENTS

| JP | 52100280 | 8/1977 |
| JP | 05045306 | 2/1993 |
| JP | 07035706 | 2/1995 |
| JP | 09178676 | 7/1997 |
| JP | 10142171 | 5/1998 |
| JP | 10227898 | 8/1998 |
| JP | 11502312 | 2/1999 |

* cited by examiner

Primary Examiner—David V. Bruce
Assistant Examiner—Hoon Song
(74) Attorney, Agent, or Firm—Adams & Wilks

(57) ABSTRACT

In a fluorescent X-ray analysis apparatus, a diffraction X-ray is removable from a sample even if it is formed of a mixture of fine crystals. A movable collimator mechanism capable of detecting only a collimate component of an X-ray optical flux is provided in a secondary X-ray path extending between a sample and an X-ray detector. Spectrum measurement is conducted on the same sample when the collimator mechanism is inserted and removed from the secondary X-ray path.

5 Claims, 4 Drawing Sheets

FLUORESCENT X-RAY ANALYSIS APPARATUS

BACKGROUND OF THE INVENTION

1. Field of the Invention

The present invention relates to a fluorescent X-ray analysis apparatus for conducting element analysis by detecting an X-ray secondarily produced from a sample when radiating an X-ray to the sample.

2. Description of the Prior Art

The fluorescent X-ray analysis apparatus is used to conduct qualitative/quantitative analysis of a sample by radiating a primary X-ray emitted from an X-ray source onto a sample and detecting a fluorescent X-ray produced from the sample, thereby obtaining a spectrum as energy intensity information. At this time, a diffraction X-ray is produced besides a fluorescent X-ray from such a material as with a crystallinity or that having been extended. This will appear as an interference peak on a spectrum to impede qualitative/quantitative analysis. As a measure to remove this, a sample rotary mechanism has conventionally been employed.

However, the effect of sample rotation upon removing diffraction X-ray is limited to a case that the sample is comparatively uniform in crystalline orientation. There is a problem that diffraction X-ray is difficult to remove in a case where the sample is random in crystalline surface such as that of a mixture of fine crystals.

SUMMARY OF THE INVENTION

In order to solve the above problem, the present invention provides a movable collimator mechanism capable of detecting only a collimate component of an X-ray optical flux on an X-ray path between a sample and an X-ray detector. A spectrum is measured on the same sample in both cases that a collimator is inserted and not inserted. At this time, if a collimator mechanism is inserted, only a secondary X-ray reaches the detector which is uniform in an angle defined between a line which connects an intersection of a primary X-ray optical flux center line and a sample surface (this is referred to as a primary X-ray radiation center) to a detection region center of the X-ray detector and the sample surface (this is referred to as an extraction angle). Also, where the collimator mechanism is not inserted, detected is a secondary X-ray having an extraction angle with a given width with a result that each spectrum is varied in diffraction X-ray peak width appearing thereon. On the other hand, because the fluorescent X-ray peak width is not affected by the extraction angle, it is possible to discriminate between a peak due to a diffraction X-ray and a peak of a fluorescent X-ray by observing two spectrums obtained. Accordingly, qualitative/quantitative analysis was made feasible free from the effect of interference due to a diffraction X-ray by analyzing a spectrum when the diffraction X-ray peak width is smaller and a collimator mechanism less in disturbance to the fluorescent X-ray peak is inserted, or by removing a diffraction X-ray peak through a simple arithmetic process for the obtained two spectrums.

DETAILED DESCRIPTION OF THE PREFERRED EMBODIMENT

An embodiment of the present invention will be described hereinunder with reference to the drawings.

Figure 1:
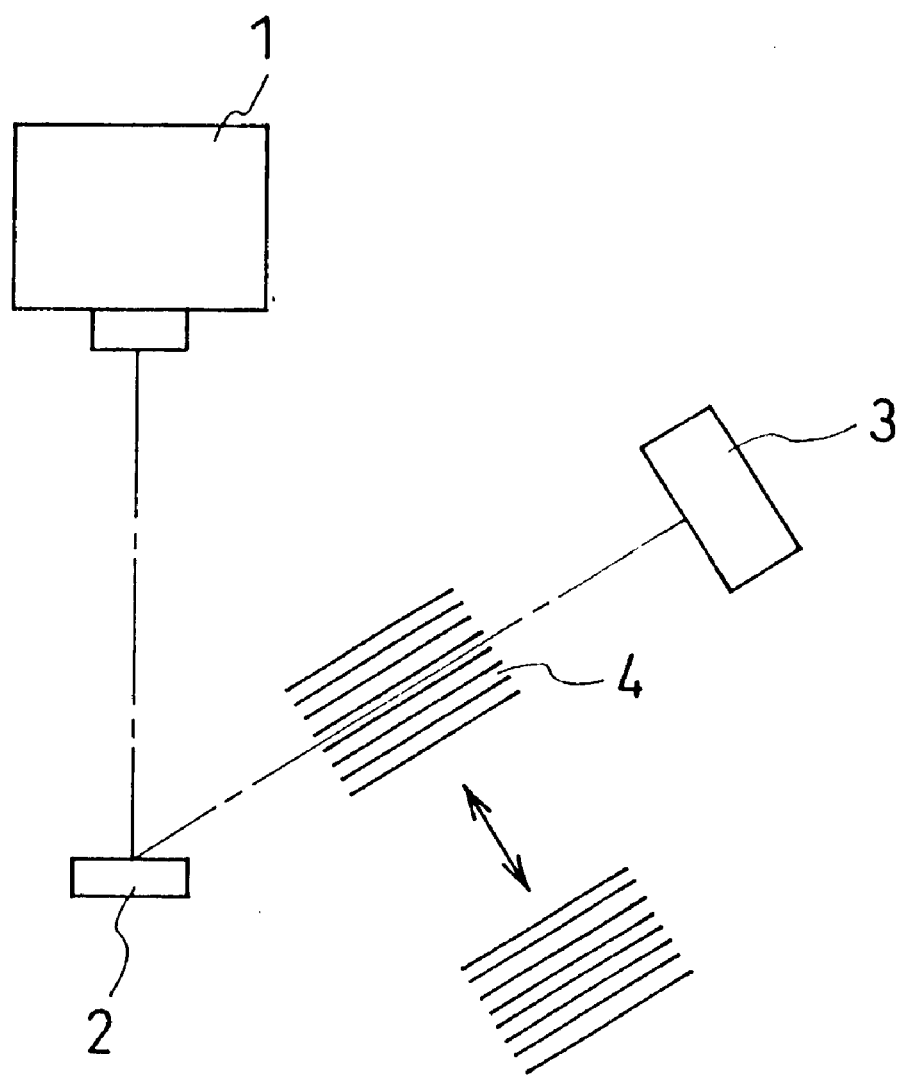
FIG. 1 is a schematic view showing a structure of a fluorescent X-ray analysis apparatus of the present invention.

Referring to FIG. 1, there is illustrated one example of an X-ray analysis apparatus to be used in the present invention. An X-ray source 1 emits an X-ray to be incident onto a sample 2. From the sample 2 a secondary X-ray is produced that includes a fluorescent X-ray and diffraction X-ray. Thereupon, a detector detects only a secondary X-ray put uniform in extraction angle by a collimator 4 arranged on an X-ray path between the sample 2 and the detector 3. In this state a spectrum is acquired, and thereafter the collimator 4 is moved out of the X-ray path to acquire a spectrum. In the apparatus with such structure, the condition that a diffraction X-ray reaches from the sample to the detector to cause a peak appearing on the spectrum is known as Bragg's formula $$n\lambda = 2d \sin \theta \quad (1)$$

where θ is the Bragg's angle. Provided that a half of an angle defined by three points of the X-ray source, the primary X-ray radiation center on the sample and detector detection region center point is given ½ as φ, we obtain $$\theta = (180° - 2\phi)/2 \quad (2).$$

Meanwhile, d is a lattice constant of a crystal forming the sample, λ is a wavelength of the diffraction X-ray, and n is an order. Accordingly, if Equation (2) is substituted into Equation (1), we obtain $$n\lambda = 2d \cos \phi \quad (3).$$

In the structure of the invention, the insertion of the collimator 4 onto the X-ray path results in narrowing the extraction angle of the secondary X-ray reaching the detector to a certain range. This is nothing more than change in the range of φ. Consequently, the diffraction X-ray will change in range of wavelength (or energy). On the other hand, the fluorescent X-ray to be produced from the sample will not be affected in energy by the range φ.

For example, FIG. 2 is a sectional view that a geometrical arrangement a secondary X-ray reaches a detector is projected onto a plane including three planes, i.e. an X-ray source, a primary X-ray radiation center on a sample and a detector detection region center point. Using this figure, explanation is made on change of the range φ. It is herein assumed for the sake of simplifying explanation that the primary X-ray is a collimate light flux. In an actual apparatus, however, the effect of spread in the primary X-ray is in a negligible extent as compared to change in range of extraction. No effect thereof will be greatly lost in the below explanation.

Figure 2A:
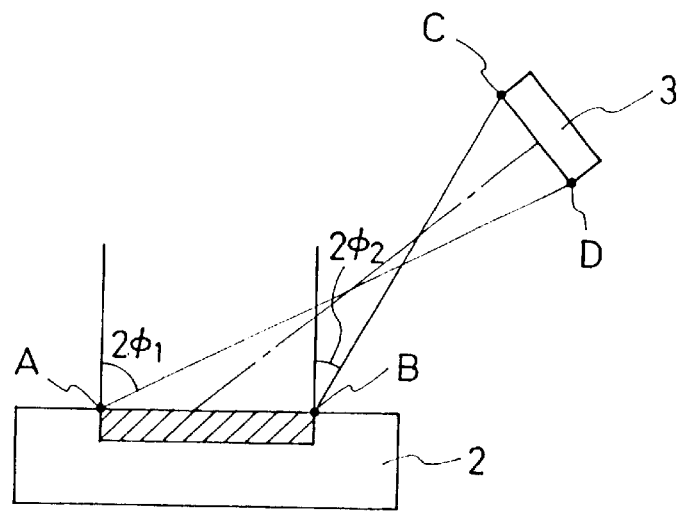
FIG. 2 is an explanatory view showing a diffraction X-ray peak producing mechanism.

FIG. 2A is a typical view for the case that the collimator lens is not inserted. The region of a sample 2 radiated by a primary X-ray is shown by hatching, from which a secondary X-ray is being produced. In the figure, the angle defined by three points, i.e. an X-ray source, a primary X-ray radiation center on the sample, a detector detection region center point, becomes a maximum for a secondary X-ray taken along a line segment AD connecting between a farthest point A from the detector in the region on the sample that the secondary X-ray is being produced and a farthest point D from the sample in a detector detection range, wherein in this case is assumed taken as $\phi 1$. Conversely, this angle becomes a minimum for a secondary X-ray taken along a line segment BC connecting between a closest point B to the detector in the region on the sample that the secondary X-ray is being produced and a closest point C to the sample in the detector detection range, wherein $\phi$ in this case is assumed taken as $\phi 2$. Accordingly, where the collimator is not inserted, then a half of the angle defined by the three point of the X-ray source, the primary X-ray radiation center on the sample and the detector detection region center point takes a range of $\phi 2 < \phi < +1$.

Figure 2B:
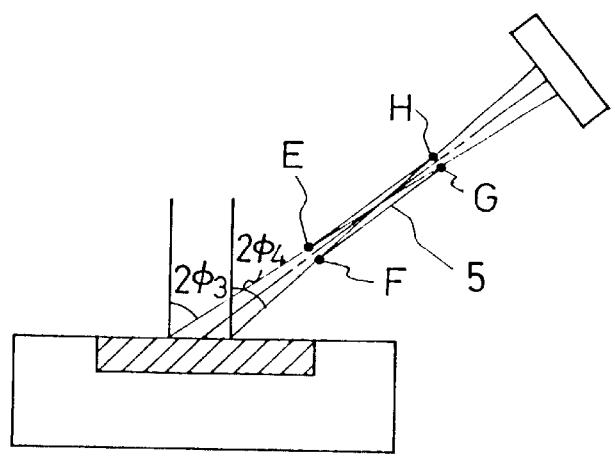

FIG. 2B is a typical view in the case that the collimator is inserted. It is herein considered on a range of $\phi$ concerning on one hollow tube including a line connecting between a primary X-ray radiation center on the sample and a detector detection region center point. In an actual apparatus, however, it may be considered that hollow tubes with the same length exist in parallel around this hollow tube 5 wherein the respective hollow tubes clearly take the same angular range. In this figure, the angle defined by three points, i.e. an X-ray source, a primary X-ray radiation center on the sample, a detector detection region center point, becomes a maximum for a secondary X-ray taken along a line segment EG connecting between a point E and a point G of the hollow tube, wherein $\phi$ in this case is assumed taken as $\phi 3$. Conversely, this angle becomes a minimum for a secondary X-ray taken along an extension of a line segment FH connecting between a point F and a point H of the hollow tube, wherein $\phi$ in this case is taken as $\phi 4$. Accordingly, where a collimator is inserted, then a half of the angle defined by the three point of the X-ray source, the primary X-ray radiation center on the sample and the detector detection region center point takes a range of $\phi 4 < \phi < \phi 3$.

Figure 3A:
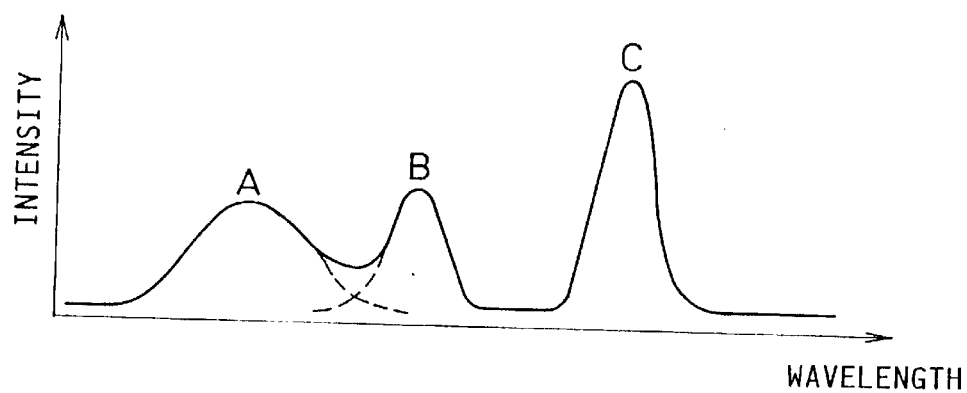
FIG. 3 is an explanatory view showing a diffraction X-ray removal mechanism.
Figure 3B:
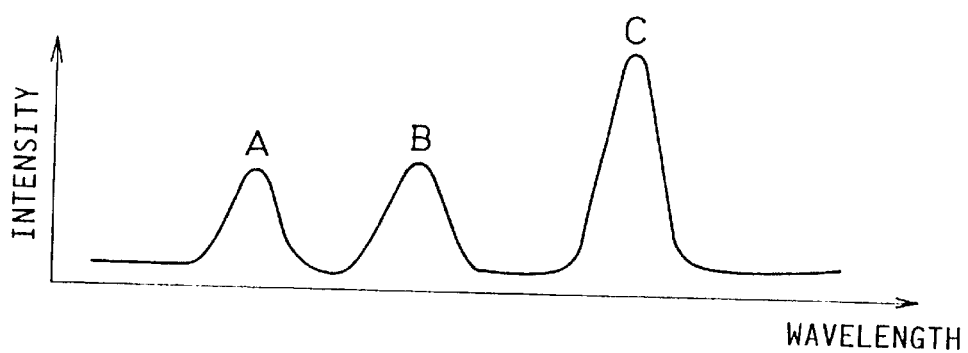

In the meanwhile, provided that D is assumed taken for a lattice constant of a crystalline structure of a sample being considered that a diffraction X-ray peak is caused, when the collimator is not inserted, a primary X-ray having a wavelength lying in a range of from $\lambda 1 = 2D (\cos \theta 1)/n$ to $\lambda 2 = 2D (\cos \theta 2)/n$ satisfies the Bragg's condition, which diffracts and reaches the detector where it is to be confirmed as a broad diffraction peak including a system wavelength resolving power on the spectrum. On the other hand, when the collimator is inserted, the wavelength range satisfying the Bragg's condition lies in a range of from $\lambda 3 = 2D (\cos \theta 3)/n$ to $\lambda 4 = 2D (\cos \theta 4)/n$. This is clearly narrow in wavelength range as compared to the case that the collimator is not inserted. FIG. 3A shows an example of a spectrum acquired in the case no collimator is inserted. Herein, peaks A, B and C are observed. Next, FIG. 3B shows a spectrum when measuring on the same sample with the collimator is inserted. It can be discriminated among the peaks A, B and C observed that the peak A narrowed in peak width is due to a diffraction X-ray while the peaks B and C without width change are due to a fluorescent X-ray. In such a case, a qualitative/quantitative analysis is made possible without encountering impediment due to a diffraction X-ray, by performing an analysis using the spectrum acquired by inserting the collimator (FIG. 3B) instead of using the spectrum having interference of the fluorescent X-ray peak B with the diffraction X-ray peak A (FIG. 3A).

Meanwhile, in also a case that a diffraction X-ray peak interferes with other fluorescent X-ray peaks despite a collimator is inserted, it is similarly possible to conduct a qualitative/quantitative analysis free from impediment due to a diffraction X-ray by using a simple peak separation technique to extract and remove only a diffraction X-ray peak.

Figure 4:
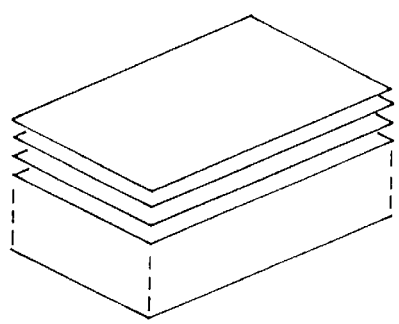
FIG. 4 is a typical view showing a parallel flat plate collimator.
Figure 5:
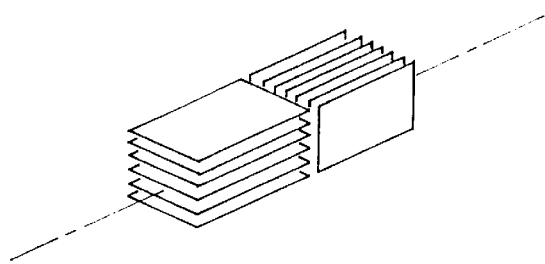
FIG. 5 is a typical view showing an arrangement in a case of using two parallel flat plate collimators.
Figure 6:
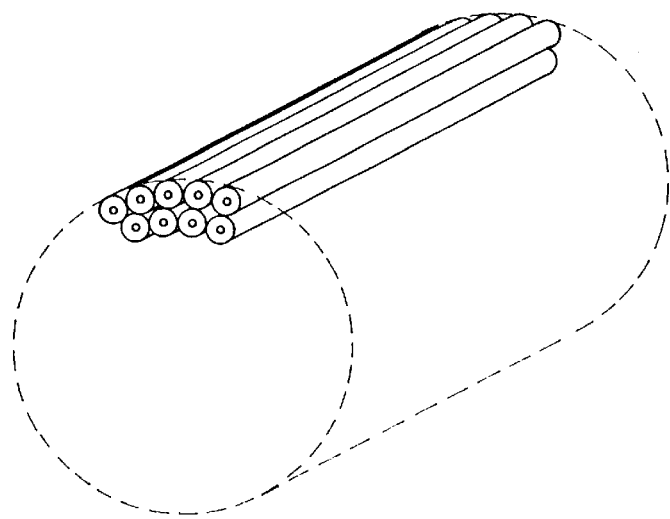
FIG. 6 is a typical view showing a poly-capillary collimator.

The collimator can use, as shown in FIG. 4, one parallel flat plate having metal foils arranged parallel at a constant interval. Alternatively, if as shown in FIG. 5 this is used two in the number for arrangement on a secondary X-ray path in a continuous and perpendicular relation to each other, there will be increase in change of diffraction X-ray peak width, thus facilitating diffraction X-ray peak detection. Furthermore, it is possible to use a poly-capillary bundled with metal or glass hollow tubes, as shown in FIG. 6.

As described above, in a fluorescent X-ray analysis apparatus for conducting element analysis by detecting an X-ray secondarily produced from a sample upon radiating an X-ray, a movable collimator mechanism capable of detecting only a collimate component of an X-ray optical flux on an X-ray path between a sample and an X-ray detector. A spectrum is measured on the same sample in both cases the collimator is inserted and not inserted. Accordingly, it is possible to remove a diffraction X-ray even where the sample is made up of a mixture of fine crystals. Thus, qualitative/quantitative analysis is feasible without encountering interfering rays.

What is claimed is:

1. A fluorescent X-ray analysis apparatus comprising:

an X-ray source for generating a primary X-ray;

a sample table for fixing a sample to be radiated by the primary X-ray;

a detector for detecting a secondary X-ray produced by the sample in response to irradiation by the primary X-ray; and a collimator mechanism removably insertable in an X-ray path between the sample and the detector for passing a secondary X-ray component having a uniform extraction angle and reducing a secondary X-ray component having a non-uniform extraction angle, the extraction angle being defined between a first line connecting an intersection of a center line of an x-ray optical flux radiated by the X-ray source with a plane of the sample table and a second line connecting a center point of a detection region of the detector with a plane of the sample table.

2. A fluorescent X-ray analysis apparatus according to claim 1; wherein the collimator mechanism comprises a parallel plate collimator having a plurality of metal thin sheets arranged in parallel and spaced apart by a small interval.

3. A fluorescent X-ray analysis apparatus according to claim 1; wherein the collimator mechanism comprises a poly-capillary bundled with metal or glass hollow tubes.

4. A fluorescent X-ray analysis apparatus according to claim 1; wherein the collimator mechanism comprises two parallel plate collimators arranged perpendicularly to each other along a path of the secondary X-ray, each plate collimator having a plurality of metal thin sheets arranged in parallel and spaced apart by a small interval.

5. A method of performing X-ray analysis comprising the steps of:

irradiating a sample with a primary X-ray;

obtaining a first spectrum by measuring a secondary X-ray emanating from the sample in response to irradiation of the sample by the primary X-ray;

inserting a collimator in a path of the secondary X-ray to allow a collimate component of the secondary X-ray to pass therethrough;

obtaining a second spectrum by measuring the secondary X-ray emanating from the sample in response to irradiation of the sample by the primary X-ray while the collimator is interposed in the path of the secondary X-ray; and performing an arithmetic process on the first and second spectrums to remove a diffraction X-ray peak.

* * * * *